United States Patent
Newport et al.

(10) Patent No.: US 10,379,167 B2
(45) Date of Patent: Aug. 13, 2019

(54) RECHARGEABLE TOOL AND BATTERY STATUS MONITORING IN AN AUTOMATED TOOL CONTROL SYSTEM

(71) Applicant: SNAP-ON INCORPORATED, Kenosha, WI (US)

(72) Inventors: Jason Newport, Conway, AR (US); David C. Fly, Maumelle, AR (US); Preston C. Phillips, Conway, AR (US); Matthew J. Lipsey, Sherwood, AR (US); Frederick J. Rogers, North Little Rock, AR (US); Joseph Chwan, Mechanicsburg, PA (US); Andrew R. Lobo, Wadsworth, IL (US); Sean W. Ryan, Pleasant Prairie, WI (US)

(73) Assignee: SNAP-ON INCORPORATED, Kenosha, WI (US)

( * ) Notice: Subject to any disclaimer, the term of this patent is extended or adjusted under 35 U.S.C. 154(b) by 0 days.

(21) Appl. No.: 15/722,494

(22) Filed: Oct. 2, 2017

(65) Prior Publication Data

US 2018/0095138 A1    Apr. 5, 2018

Related U.S. Application Data

(60) Provisional application No. 62/403,549, filed on Oct. 3, 2016.

(51) Int. Cl.
*G06Q 10/08*    (2012.01)
*G01R 31/3842*  (2019.01)
(Continued)

(52) U.S. Cl.
CPC ....... *G01R 31/3842* (2019.01); *A61N 1/3931* (2013.01); *G01R 31/3646* (2019.01);
(Continued)

(58) Field of Classification Search
CPC ................................................... H02J 7/0044
(Continued)

(56) References Cited

U.S. PATENT DOCUMENTS 6,218,796 B1    4/2001    Kozlowski
2007/0090788 A1 4/2007    Hansford et al.
(Continued)

FOREIGN PATENT DOCUMENTS

DE    102014217965 A1    3/2016
WO    2014/189972 A1    11/2014

OTHER PUBLICATIONS

International Search Report and Written Opinion issued in International Application No. PCT/US2017/054721, dated Dec. 13, 2017.

*Primary Examiner* — Edward Tso
*Assistant Examiner* — Ahmed H Omar
(74) *Attorney, Agent, or Firm* — McDermott Will & Emery LLP

(57) ABSTRACT

An automated tool control system provides both inventory control of items stored in the system and monitoring of the charging status of rechargeable inventory items such as tools and batteries stored in the system. For these purposes, the tool control system includes storage locations for storing tools and other inventory items, and the storage locations include at least one storage location located in a charger operative to charge a rechargeable tool, battery, or battery pack disposed therein. In operation, the tool control system may monitor the charging status of any tool, battery, or battery pack disposed in the storage location of the charger through monitoring of battery status indicators of the tool, battery, battery pack, or charger; through monitoring of current or voltage drawn by the tool, battery, battery pack,
(Continued)

or charger; or through wired or wireless communication with a communication enabled tool, battery, battery pack, or charger.

21 Claims, 7 Drawing Sheets

(51) Int. Cl.
G01R 31/36 (2019.01)
H01M 10/48 (2006.01)
A61N 1/39 (2006.01)
H02J 7/00 (2006.01)
G06K 9/78 (2006.01)
G06K 9/00 (2006.01)

(52) U.S. Cl.
CPC .............. *G06K 9/00* (2013.01); *G06K 9/78* (2013.01); *G06Q 10/087* (2013.01); *H01M 10/48* (2013.01); *H02J 7/0004* (2013.01)

(58) Field of Classification Search
USPC .......................................................... 320/107
See application file for complete search history.

(56) References Cited

U.S. PATENT DOCUMENTS

| | | | |
|---|---|---|---|
| 2008/0088454 A1* | 4/2008 | Flores ................ | G08B 13/2457 340/572.4 |
| 2010/0121482 A1* | 5/2010 | Jackson ............... | G06Q 10/087 700/217 |
| 2014/0023264 A1* | 1/2014 | Branch .................... | G06K 9/78 382/141 |
| 2014/0062700 A1* | 3/2014 | Heine ................ | G08B 13/2462 340/572.1 |
| 2014/0253021 A1* | 9/2014 | Luke .................... | H02J 7/0013 320/107 |
| 2014/0350716 A1* | 11/2014 | Fly ........................ | G06F 1/3212 700/215 |
| 2017/0244262 A1 | 8/2017 | Schadow et al. | |

* cited by examiner

RECHARGEABLE TOOL AND BATTERY STATUS MONITORING IN AN AUTOMATED TOOL CONTROL SYSTEM

CROSS-REFERENCE TO RELATED APPLICATION

This application claims the benefit of U.S. Provisional Application No. 62/403,549, filed on Oct. 3, 2016, the disclosure of which is incorporated herein in its entirety.

TECHNICAL FIELD

The present subject matter relates to techniques and equipment to monitor the status of rechargeable tools, batteries, and battery packs, including the charge status of the batteries, in an automated tool control system.

BACKGROUND

Due to a continuing drive to improve efficiencies, eliminate waste and downtime, improve product safety and quality, in addition to meeting increasingly accepted foreign object debris (FOD) regulations, the implementation and use of automated asset management systems is growing in aerospace, manufacturing, research, transportation and railroad, food preparation, mining, microelectronics, and other industries.

Currently available automated asset management systems utilize a variety of technologies to identify objects issued from and returned to a secure storage device or an enclosed secure storage area. Examples for a secure storage device may include a tool box or tool locker and an example of a secure enclosed area may include a tool crib or walk in tool locker. These technologies currently may include, but are not limited to manual tracking with paper forms, manual tracking with data input into computer programs, camera imaging, passive RFID (radio frequency identification), optical code scanning, optical tag scanning, and the like.

These systems share the same basic goals which include identifying the individual who received and or returned the object, identifying the object which is being issued or returned, placing a time stamp on each transaction within the system and storing item and user data in a database.

Each of the technologies listed above has advantages and disadvantages when used in an automated asset management system. For example, the imaging system does not generally distinguish between different items that may be visually identical to each other. RFID based systems have limitations on the size of the tools as some tools are too small to have RFID chips placed on them.

A challenge that remains unaddressed relates to the storage and tracking of portable rechargeable tools and/or spare batteries and battery packs for such tools. Use of these devices is fast becoming ubiquitous within the industries mentioned above.

SUMMARY

The teachings herein alleviate one or more of the above noted problems with the storage and tracking of portable rechargeable tools and/or spare batteries and battery packs for such tools.

In accordance with the principles of the disclosure, an automated tool control system includes a plurality of storage locations, a charger associated with one storage location of the plurality of storage locations, and a processor and sensing device configured to determine the presence or absence of inventory items in the plurality of storage locations. The plurality of storage locations are configured to store inventory items including at least one rechargeable inventory item. The charger is configured to charge the at least one rechargeable inventory item when the at least one inventory item is present in the one storage location. The processor is further configured to determine presence of the at least one rechargeable inventory item in the one storage location associated with the charger, and to monitor a charging status of the at least one rechargeable inventory item.

In accordance with further principles of the disclosure, a method for monitoring a charging status of a rechargeable inventory item includes determining, using a processor and sensing device of an automated tool control system, presence or absence of the rechargeable inventory item in a plurality of storage locations of the automated tool control system. Upon determining presence of the rechargeable inventory item in the plurality of storage locations, presence is determined of the rechargeable inventory item in one storage location associated with a charger configured to charge the rechargeable inventory item when the at least one inventory item is present in the one storage location. Upon determining presence of the rechargeable inventory item in the one storage location associated with the charger, a charging status of the rechargeable inventory item is monitored.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
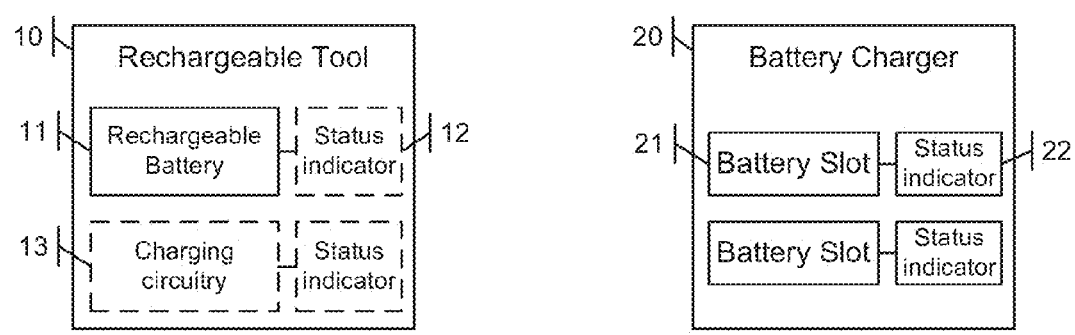
FIG. 1 shows a high-level block diagram of a rechargeable tool and a battery charger as may be used in accordance with the tool control systems described herein.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various methods and systems disclosed herein relate to the monitoring of the status of rechargeable tools and batteries in automated tool control (ATC) systems, including the monitoring of the charging status of the tools and batteries. For example, the methods and systems can monitor the presence or absence of a tool or battery in the ATC system and, when the tool or battery is determined to be present in the ATC system, monitor the charging status of the tool or battery. In turn, the methods and systems can maintain and store a charging and discharging history of the tool or battery, and estimate a current charging status of the tool or battery based on the charging history, any current monitored charging status, and any check-out or usage history.

In various embodiments, the methods and systems monitor the charging status of the tool, battery, or battery pack using one or a combination of approaches. For example, the methods and systems may rely on a sensing device or system, such as a camera, to visually monitor the charging status of the tool or battery by monitoring a color (e.g., red vs. green) and/or status or activity (e.g., off vs. steadily lit vs. blinking) of a battery status or battery level indicator of the tool, battery, battery pack, or associated charger. The methods and systems may alternatively or additionally rely on a sensing device or system, such as a current or voltage sensor, to sense a current or voltage being supplied to the tool, battery, or associated charger, and infer the charging status of the tool or battery from the sensed current or voltage. The methods and systems may further rely on a sensing device or system, such as a communication interface, to communicate across a wired or wireless communication link with a communication interface of a tool, battery, or associated charger having an internal sensing system for monitoring the charging status of the tool or battery, and to be provided with the charging status of the tool or battery across the communication link.

Based on the monitored charge status of the tool or battery, the methods and systems can estimate a current charge level or status of the tool or battery. For example, the tool or battery may be estimated to be fully charged (or near full charge) based on the visually monitored charging status of the tool or battery (e.g., upon determining that a green battery status indicator indicating a full charge is lit), based on the length of time during which the tool or battery has been charging (e.g., upon determining that the tool or battery has been charging for more than a predetermined amount of time, such as 4 hours), based on the current drawn by the tool or charger having transitioned from a high value (e.g., indicating a charging current is being drawn) to a low value (e.g., indicating that a charging current is no longer being drawn), or the like.

Reference now is made in detail to the examples illustrated in the accompanying drawings and discussed below.

FIG. 1 shows an illustrative rechargeable tool 10, such as a portable power tool or other inventory device or item having a rechargeable battery 11 therein. The rechargeable tool 10 includes one or more rechargeable batteries 11 or rechargeable battery packs that can be removably inserted or mounted into the tool 10 or device. The batteries 11 or battery packs (generally references as "batteries" herein) can be removable from the tool 10 or device, such that a discharged battery can be readily replaced with a fully recharged battery in the tool 10.

A charger 20 is generally separate from the tool 10 or device and includes one or more slots 21 into which a rechargeable battery 11 or battery pack can be inserted in order to recharge the battery or battery pack. In some examples, optional charging circuitry 13 is provided within the tool 10 itself to allow recharging of a battery or battery pack while it is inserted or mounted into the tool 10 by connecting the tool to a power source or charger. The charger 20 and/or charging circuitry 13 charges the battery or battery pack when power is provided thereto, such as when the charger 20 or charging circuitry 13 is plugged in to an electrical outlet and receives power from the outlet.

A status indicator 22 associated with each battery slot 21 may indicate a current state of operation of the battery slot or a current state of charging of a battery mounted into the battery slot. The status indicator 22 can take the form of one or more LEDs whose color (e.g., green or red) and status (e.g., off, flashing, or steadily lit) are indicative of the current state of operation of the battery slot or a current state of charging of a battery mounted into the battery slot. For example, a red flashing status indicator 22 may indicate that the battery slot is currently charging a battery mounted therein; a red steadily list status indicator 22 may indicate a malfunction of the charger or battery, such as a bad connection or other malfunction preventing charging of the battery; and a green steadily list status indicator 22 may indicate a fully charged battery. Similarly, an optional status indicator 12 associated with a battery 11 or battery pack mounted in the tool 10 indicates a current state of operation or a current state of charge of the battery 11 mounted into the tool 10. The status indicator 12 can take the form of one or more LEDs. The status indicator 12 may be located on the tool 10 and be indicative of a status of a battery currently mounted in the tool 10, or the status indicator 12 may be located directly on the battery 11 or battery pack.

Figure 2A:
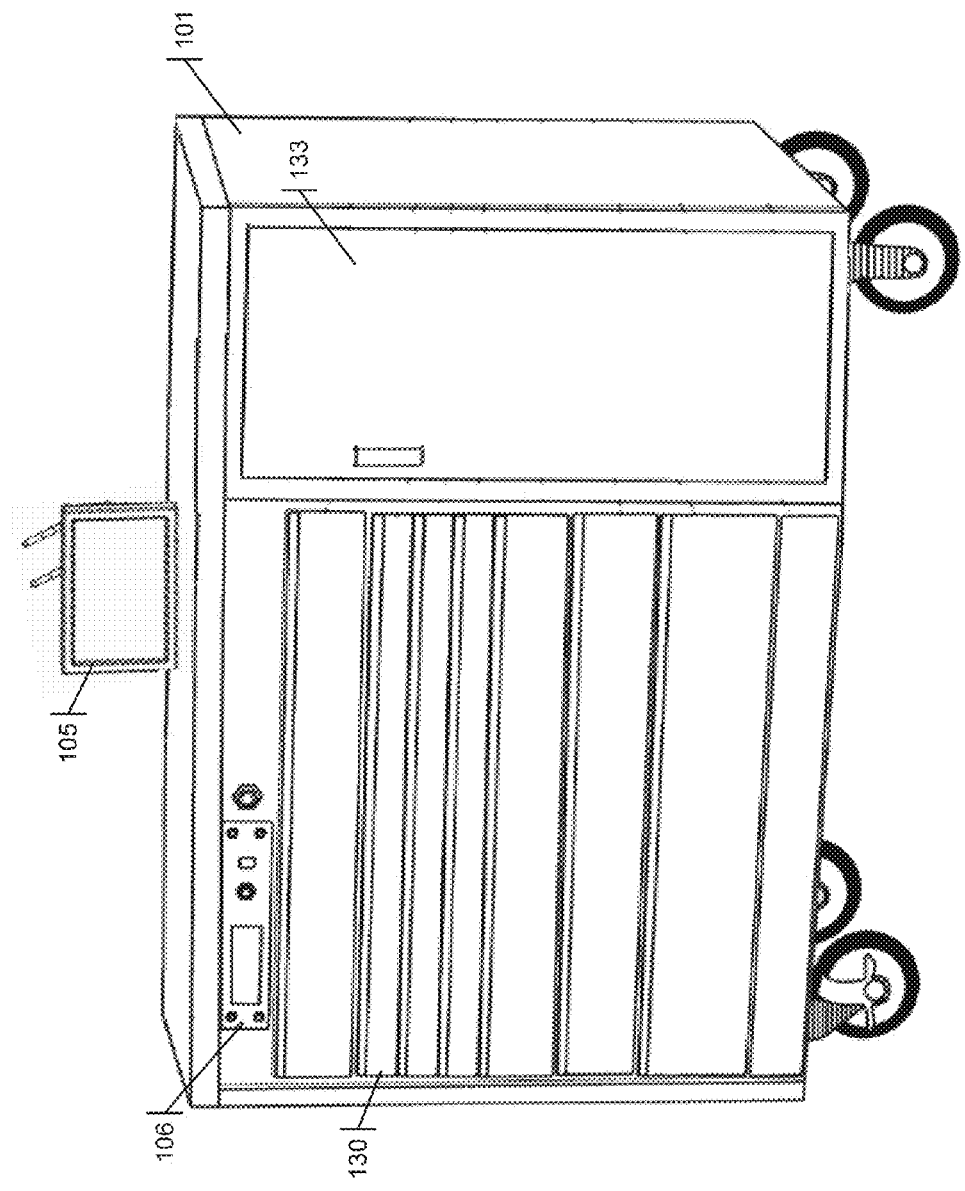
FIGS. 2A, 2B, and 2C show an illustrative automated tool control system, a drawer thereof, and a cabinet thereof that provide the inventory control and battery status monitoring functionalities described herein.

Each of the tool 10, the batteries 11, battery packs, or other rechargeable inventory item (and any additional or spare batteries or battery packs), and the charger 20 may advantageously be stored in an automated tool control system such as that shown in FIG. 2A, and use and location of each these devices may advantageously be tracked by the automated tool control system.

Figure 2B:
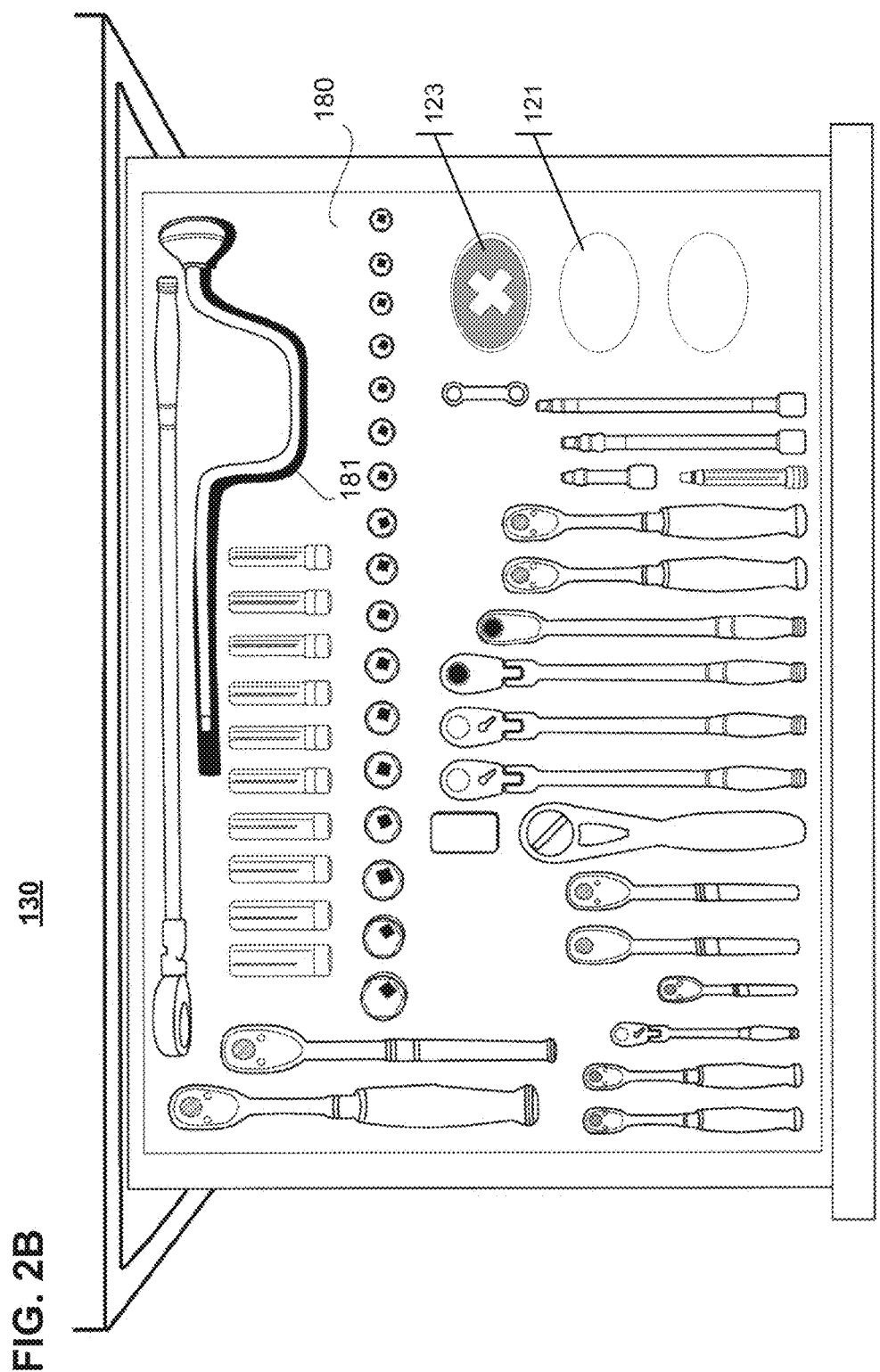

Due to the physical size of the chargers themselves and their increased size when coupled with batteries or battery packs, the chargers generally do not fit well in drawers of a standard automated tool control (ATC) system tool box such as those shown in FIGS. 2A and 2B. In many cases, the rechargeable tools 10 also large and bulky and may not readily fit into a standard drawer 130 of an ATC system tool box.

In addition, the portable tool battery chargers also may require electrical power (e.g., alternating current (AC) power) to be provided to them to operate. Providing electrical power to a charger stored in a drawer of a standard automated tool control system tool box may be difficult.

To address these issues, an improved automated tool control system is provided herein. The improved automated tool control system includes both storage drawers and a side storage cabinet in which electrical power is provided to provide battery charging capabilities within the ATC tool box.

Additionally, the improved automated tool control system is equipped with sensing and monitoring technology to gather available data pertaining to portable tools stored therein, pertaining to batteries and battery packs stored therein, and pertaining to the operations of chargers stored therein. The sensing and monitoring technology gathers battery and charger related data, and provides monitoring information to system users and administrators.

Figure 2C:
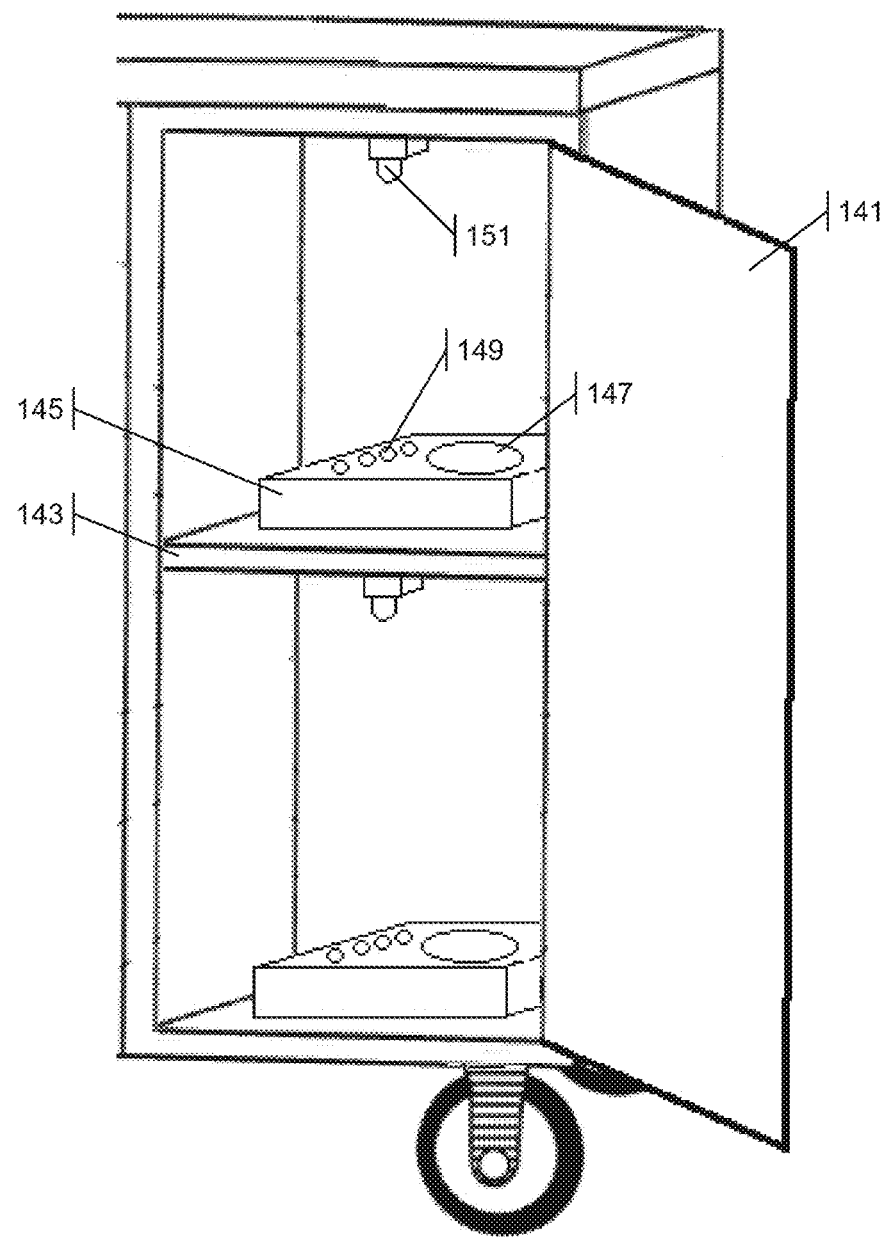

For example, as shown in FIGS. 2A-2C, the improved automated tool control system 100 includes a physically defined three dimensional casing 101, such as a tool crib or object storage device, which defines a secure internal space serving as a container in which the tools or other devices are stored. The tools and devices can be issued and/or returned from the casing 101, and more specifically from one or more drawers 130, cabinets 133, or other storage spaces of the casing 101. The casing 101 may further store or contain a storage device from which a tool or device is issued and/or returned.

As shown in FIG. 2A, the improved automated tool control system 100 can include both one or more drawers 130 and/or one or more cabinets 133 for storage of tools or other inventory items including rechargeable tools, rechargeable batteries, rechargeable battery packs, chargers, and the like. Additionally, an access control device 106, such as a card reader, can be used for verifying identity and authorization levels of users intending to use the tool control system 100 and retrieve tools or inventory items therefrom. The tool control system 100 can further include a user interface enabling visual or audio messages, alerts, or other information to be communicated to a user. The user interface can include a user input interface which can take the form of a touch-screen interface enabling a user to provide input commands via display screen 105, or the form of a keyboard, a track-pad, a motion sensor, a tablet, or the like.

While the automated tool control systems are illustratively shown herein as tool boxes (see, e.g., FIG. 2A), the tool control systems can take different forms which may or may not include a tool box. For example, while the casing 101 is shown in FIGS. 2A-2C as being a tool box with drawers 130 and a side cabinet with shelves 143, the casing can more additionally or alternatively be equipped with storage hooks, hangers, doors, and the like. The casing 101 can be a tool box, a locker, a safe, a closet, a vending machine, a barrel, a crate, or other storage container. Furthermore, automated tool control systems may more generally be referenced to as tool storage systems or automated asset management systems.

The access control device 106 may work in concert with at least one electronically controlled locking mechanism for securely locking the drawers 130 and doors 141 of any cabinets 133. The access control device 106, such as a card reader, along with a processor and a memory storing executable program instructions, electronically identifies a user requesting access to the tool storage system 100, determines an authorization level for the user, and selectively provides access to the secure area of the toolbox 101 based on the determined authorization level. The processor and memory storing executable program instructions are operative to identify predetermined authorized access levels to the system and allow or deny physical access by the user to the storage system 100 based on those predetermined authorized levels of access. The access control device 106 used to electronically identify the user requesting access may use any of the following technologies, and others not mentioned, individually or in combination: (a) RFID proximity sensors with cards; (b) magnetic strip (magstripe) cards and scanners; (c) barcode cards and scanners; (d) common access cards and readers; (e) biometric sensor ID systems, such as (e1) facial recognition; (e2) fingerprint recognition; (e3) handwriting analysis; (e4) iris recognition; (e5) retinal scan; (e6) vein matching; (e7) voice analysis; and/or (e8) multi-modal biometric systems.

FIG. 2B illustratively shows the contents of a drawer 130 of the tool control system 100. Each storage drawer 130 includes storage locations, such as cutouts 181 in a foam base 180, for storing tools. Each storage location (e.g., cutout) is specifically contoured and shaped for fittingly receiving a tool or other inventory item with a corresponding shape. Some cutouts 121 may be configured for storing batteries or battery packs, such as the battery pack 123 shown in the figure.

As shown in FIG. 2A, the tool storage system 100 can include one or more cabinets 133. Detail of one illustrative cabinet 133 is shown in FIG. 2C. The cabinet includes a door 141 that is releasably opened to provide controlled access to a cavity in which one or shelves 143 or drawers are mounted. As shown, a battery charger 145 is provided on one shelf 143, and is provided with AC power for operation. The battery charger 145 includes a battery or battery pack slot or mounting location 147 in which a tool, battery, or battery pack can be inserted (or mounted) for charging. Additionally, one or more status indicators 149 provide a visual indication of the current charging status of any tool, battery, or battery pack mounted in the charger 145. Additionally, the cabinet 133 includes one or more sensors 151, such as one or more cameras, that are operative to capture sensing data relating to the presence of absence of any tools, batteries, battery packs, and/or chargers from the cabinet 133. The sensors 151 may also be operative to capture information relating to the charging status of tools, batteries, or battery packs in the cabinet 133.

While not described in detail herein, the automated tool control system 100 includes automated tool control (ATC) functionalities such as those described in U.S. Pat. No. 9,741,014, which issued Aug. 22, 2017 and is hereby incorporated by reference in its entirety. In particular, the automated tool control system 100 includes a plurality of storage locations for storing objects, at least one sensing system configured to sense presence or absence of the objects in the plurality of storage locations, a processor, and a non-transitory machine readable recording medium storing program instructions. The at least one sensing system senses data indicative of the presence or absence of inventors objects (e.g., tools, batteries, and battery packs), and may include sensors such as a camera capturing images of storage locations in which the inventory objects may be present or from which inventory objects may be absent. The sensing system can include various additional or alternative sensors, such as a sensor (e.g., a switch) that produces a sensing signal indicative of whether an inventory object is present (e.g., a contact switch that is depressed by the inventory object when present; a capacitive sensor that senses presence of a metallic inventory object in its vicinity, or the like); a radio frequency identification (RFID) sensor that communications with an RFID tag disposed on the inventory object when the object is within a communication range of the sensor such as within the tool control system; or the like. In operation, the automated tool control system 100 performs a scan of the storage locations using the sensing system, and determines the presence or absence of any inventory objects in the plurality of storage locations using sensing data obtained by the sensing system (e.g., image data, switch output signals, received RFID signal data, or the like).

Figure 3A:
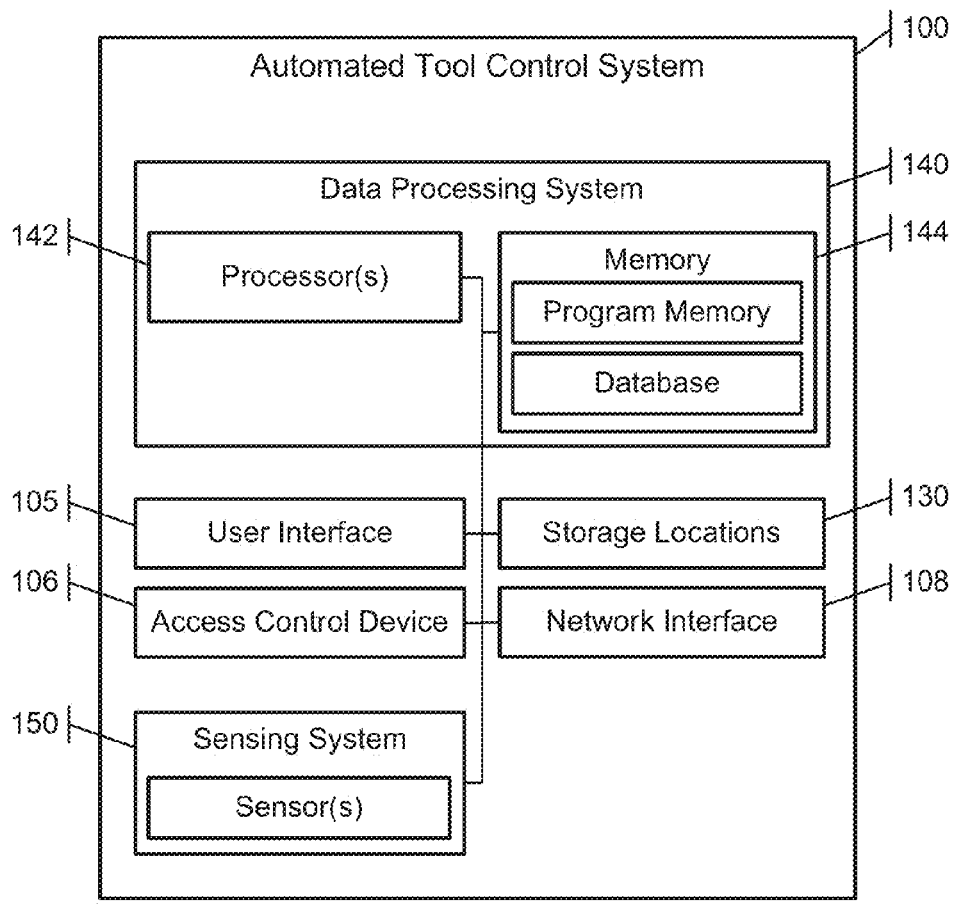
FIGS. 3A and 3B show high-level functional block diagrams of an automated tool control system and of sensing systems thereof.

FIG. 3A is a block diagram showing components of the automated tool control system 100. As shown in FIG. 3A and discussed above, the automated tool control system 100 includes storage locations 130 (e.g., cutouts 181, shelves 143, and/or battery slots 21/147), a user interface 105, an access control device 106, and a network interface 108. The storage locations 130 may be located in one or more storage drawers 130, on one or more shelves 143, in one or more cabinet doors 141, as battery slots 21/147 in charger(s) 20, or the like. The user interface 105 may include one or more user input/output devices, such as a display (e.g., a touch-sensitive display), a keyboard, a mouse or touchpad, a speaker and/or microphone, or the like. The access control device 106 may include one or more of a card reader (e.g., identification card reader), an iris scanner, a locking mechanism, an alarm, or the like. The network interface 108 enables the system 100 to communicate across one or more wired or wireless networks with other network automated tool control systems, other automated asset management or tool storage systems, or an asset management server that may be used to monitor the operation of and inventory status of multiple tool control systems.

Automated tool control system 100 further includes a data processing system 140, such as a computer, for processing sensing data received from one or more sensing system(s) 150. The data processing system 140 is equipped with a processor and stored executable program instructions for configuring the system 100 to communicate electronically directly or through a network with sensing system(s) 150 and obtain data from sensors of the sensing system(s) 150 relative to the presence or absence, location, or activity data of objects stored within the three dimensional casing 101.

For purposes of inventory control, the data processing system 140 uses the sensing data to determine inventory conditions. In various examples, the data processing system 140 processes images captured by an image sensing device of the sensing system 150, processes RFID signals captured by RFID antennas and transceivers of the sensing system 150, and/or processes other sensing signals received by other sensing systems 150. The data processing system 140 includes one or more processors 142 (e.g., micro-processors) and memory 144. The memory 144 includes a program memory storing program instructions for causing the automated tool control system 100 to perform inventory control functions and battery status monitoring functions. The memory 144 includes a database of tool information, which may include tool identifiers, tool images, tool tag information (e.g., for RFID or barcode tags), tool inventory status, and the like. The program instructions further cause the system 100 to communicate electronically directly or through a network with sensors of the sensing system 150 and obtain data from the sensors relative to the presence or absence of objects within the tool control system. Images, tag information, RFID signals, and other sensing signals captured or received by the sensing system 150 are processed by the data processing system 140 for determining an inventory condition of the system 100 and/or of each storage drawer (e.g., 130) or cabinet (e.g., 133).

Additionally, to perform the battery monitoring functions described above and in further detail below, the data processing system 140 receives sensing data monitored by sensors of the sensing system 150 that relate to the charging status of rechargeable tools, batteries, and battery packs. Such sensing data can include color (e.g., red or green) and/or activity (e.g., on, off, or blinking) of status indicators attached to tools, batteries, battery packs, and/or battery chargers disposed in the three dimensional casing 101. Status indicators may be light emitting diodes (LEDs) or other lights, digital displays, or other visual indicators configured to provide users with visual indications of a tool's, battery's, or battery pack's charge status (e.g., fully charged, partially charged, or fully discharged). Other sensing data may be captured by the sensing system 150 depending on the type of sensing system 150, as further described below.

Figure 3B:
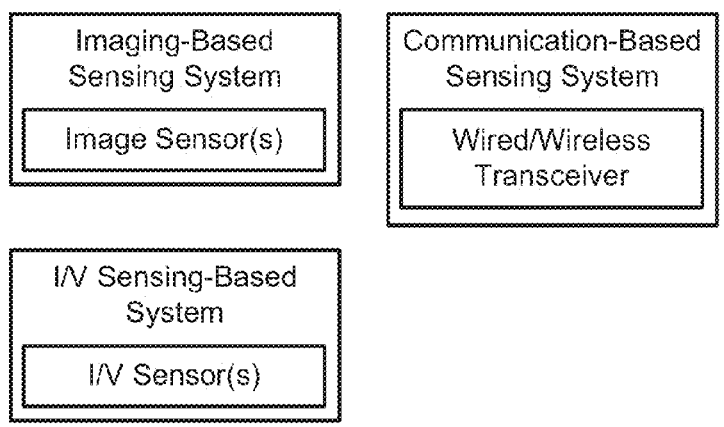

Various illustrative examples of sensing systems 150 that may be used in the automated tool control system 100 are shown in FIG. 3B. For example, an imaging-based sensing system may include one or more image sensor(s), such as lens-based cameras, CCD cameras, CMOS cameras, video cameras, or other types of devices that captures images. In examples including multiple cameras, the cameras may have different fields of view that may overlap with each other at the margins. For example, different cameras may have fields of view covering different drawers 130, shelves 143, or cabinets 133, and/or fields of view covering different portions of a same drawer, shelf, or cabinet. In operation, the imaging-based sensing system may rely on images of the drawers, shelves, or cabinets and/or objects stored in memory 144 to determine inventory conditions and/or to determine charging status of tools and batteries. The imaging-based sensing system can also be used to determine tool, battery, and charger malfunctions that are identified through a status indicator of the tool, battery, or charger. For example, if a battery, tool, or charger is configured to communicate fault conditions through a status indicator (e.g., through the display of a steady red indicator to indicate a bad connection between a charger and a tool or battery, to indicate a fault condition in the tool or battery or charger, or the like), the imaging-based sensing system can determine the fault condition based on its monitoring of the status indicator and, in turn, the processing system of the automated tool control system can log the fault condition in the database and report the fault condition to a user or administrator.

FIG. 3B also shows examples of other types of sensing systems 150. For example, a current (I) and/or voltage (V) (I/V) sensing-based system may be used to measure a current or voltage being drawn by a tool, battery, or battery charger while the tool, battery, or battery mounted in the charger is being recharged. The I/V sensing-based system can include current and/or voltage sensors, including inductive, resistive, or capacitive sensors, connected to wires supplying power to the tool, battery, or battery charger, and may provide data signals indicative of the amplitude of current and/or voltage being supplied over time. The automated tool control system 100 may, for example, use the data on current drawn by each charger to determine the charge status of any battery or battery pack currently mounted in the corresponding charger. For example, if a charger is drawing a high current (e.g., a current above a predetermined threshold), the processing system 140 may determine that the battery or battery pack currently mounted in the charger is currently charging and is therefore not fully charged; in contrast, when the charger begins drawing a much lower current or no current (e.g., a current below the predetermined threshold), the processing system 140 may determine that the battery or battery pack currently mounted in the charger is fully charged.

As another example, a communication-based sensing system may be used to obtain sensing data including information on charging status of a tool, battery, or battery charger. The communication-based sensing system can also be used to obtain sensing data including information on battery performance (including information on changes in battery capacity) or information on charging faults from a tool, battery, or charger. The communication-based sensing system relies on a wired or wireless communication transceiver of the sensing system 150 establishing a communication link with a communication transceiver of the tool or battery charger, and receiving information on battery charging status from a microcontroller of the tool (e.g., from charging circuitry 13 of a tool 10) or battery charger (e.g., from a microcontroller controlling the status indicator 22 of the battery charger 20) across the established communication link. The communication link can further be used to obtain information on battery performance, including information on changes in battery capacity or battery faults, from a microcontroller mounted in the battery or tool. For example, the communication link can be a direct communication link between the sensing system 150 and the microcontroller of the battery or tool, or the communication link can be used to relay communications between the sensing system 150 and a charger that itself communicates directly with the microcontroller of the battery or tool. The information on battery performance may be collected by the microcontroller of the battery or tool during use of the battery, such as during operation of a tool having the battery mounted therein. The battery performance information can include information on battery capacity, power output, temperature (including maximum or minimum temperatures), detected fault conditions, or the like.

In various embodiments, the same or different sensing system(s) 150 can be used in a same automated tool control system 100 for purposes of inventory control and battery status monitoring. For instance, an imaging-based sensing system may be used for both purposes, and a same set of sensors (e.g., cameras) may be used for both purposes. In other embodiments, different sensing system(s) 150 are used for different purposes. By way of non-limiting example, an RFID-based sensing system may be used for inventory control purposes while an I/V sensing-based system may be used for battery status monitoring.

Based on the sensing data obtained from the sensors of the sensing system 150, the processing system 140 maintains a database of battery status monitoring information. The database may include the following data gathered by the processing system 140 using the sensing data provided by the sensing system 150: (a) time stamps associated with each respective tool, battery, battery pack, and battery charger indicating times at which the tool, battery, battery pack, or battery charger was issued from and/or returned to the automated tool control system 100; (b) physical location of each tool, battery, battery pack, and battery charger within the tool control system, for example indicating whether the tool, battery, and battery pack is stored in a particular drawer (or a particular storage location thereof), in a particular cabinet (or a particular storage location thereof), in the charger (or a particular battery slot thereof), or at another storage location within the automated tool control system 100; (c) time stamps for movement of the tool, battery, or battery pack from the charger to another storage location within the automated tool control system 100 and/or from a storage location in the automated tool control system 100 to the charger; (d) data indicating the "name" and other identifying information (e.g., bar code, serial number, or other unique identifier) of the tool, battery, or battery pack; (e) data specifying the name of the automated tool control device the object (battery, battery pack, charger, portable tool) is stored in (e.g., in embodiments in which an automated tool control system includes multiple control devices); (f) data indicating the color of status indicator lights on chargers, tools, or batteries including time stamps identifying time periods of activity of each light; (g) data indicating activity (e.g., on vs. off; blinking vs. steady) of status indicators (e.g., LEDs or lights) on chargers, tools, and/or batteries and battery packs including time stamps identifying time periods of activity of each light; (h) data identifying the user issuing and returning each object from or to the automated tool control system; and/or (i) where applicable, electronically provided data from "Smart" batteries and/or "Smart" chargers including data on current charge level, number of charge/discharge cycles that the tool, battery, or battery pack has undergone, serial number and/or other unique identifier of the tool, battery, or battery pack, temperature of the tool, battery, or battery pack, as well as other battery performance information as described herein. Other data or information, such as that detailed in U.S. Pat. No. 9,352,905 ("Battery monitoring in a networked inventory control system") which is hereby incorporated by reference in its entirety, may also be stored including voltage and/or current sensing data (e.g., output current or voltage of the tool or battery, input current or voltage of the tool or battery), performance data, or the like.

As discussed in relation to FIG. 3B, various types of sensing systems may be used within the automated tool control system 100 and may include one or more of the following without being limited thereto: (a) optical or imaging-based identification sensors, such as (a1) sensors (e.g., cameras) configured to recognize or capture images of unique identifiers encoded in tags affixed to objects present in the tool control system, (a2) sensors (e.g., imaging sensor, line scanner, or camera) configured to recognize or capture images of one dimensional (1-d) barcodes or two dimensional (2-d) barcodes affixed to objects present in the tool control system, (a3) camera or other imaging systems configured for machine vision identification of objects, including sensors operative in the ultraviolet (UV), infrared (IR), or visible ranges of wavelengths, and/or (a4) sensors configured for laser scanning; (b) radio frequency (RF) identification sensors, such as (b1) sensors for reading RF identification (RFID) tags affixed to and/or embedded in tools, including active RFID tags and/or passive RFID tags, and/or (b2) other RF technologies used in similar manner (e.g., sensors operating according to communication standards including Ruby, Zigbee, Wifi, or the like); (c) transceivers for establishing wired or wireless electronic communication connections to tools, batteries, or battery chargers, such as (c1) transceivers configured to communicate through wired communication links with tools, batteries, or other inventory items having attached/embedded connectors for wired communication with the tool control system, and/or (c2) transceivers configured for wireless communication connections to tools, batteries, or other inventory items such as "smart" tools having embedded wireless capabilities.

Figure 4:
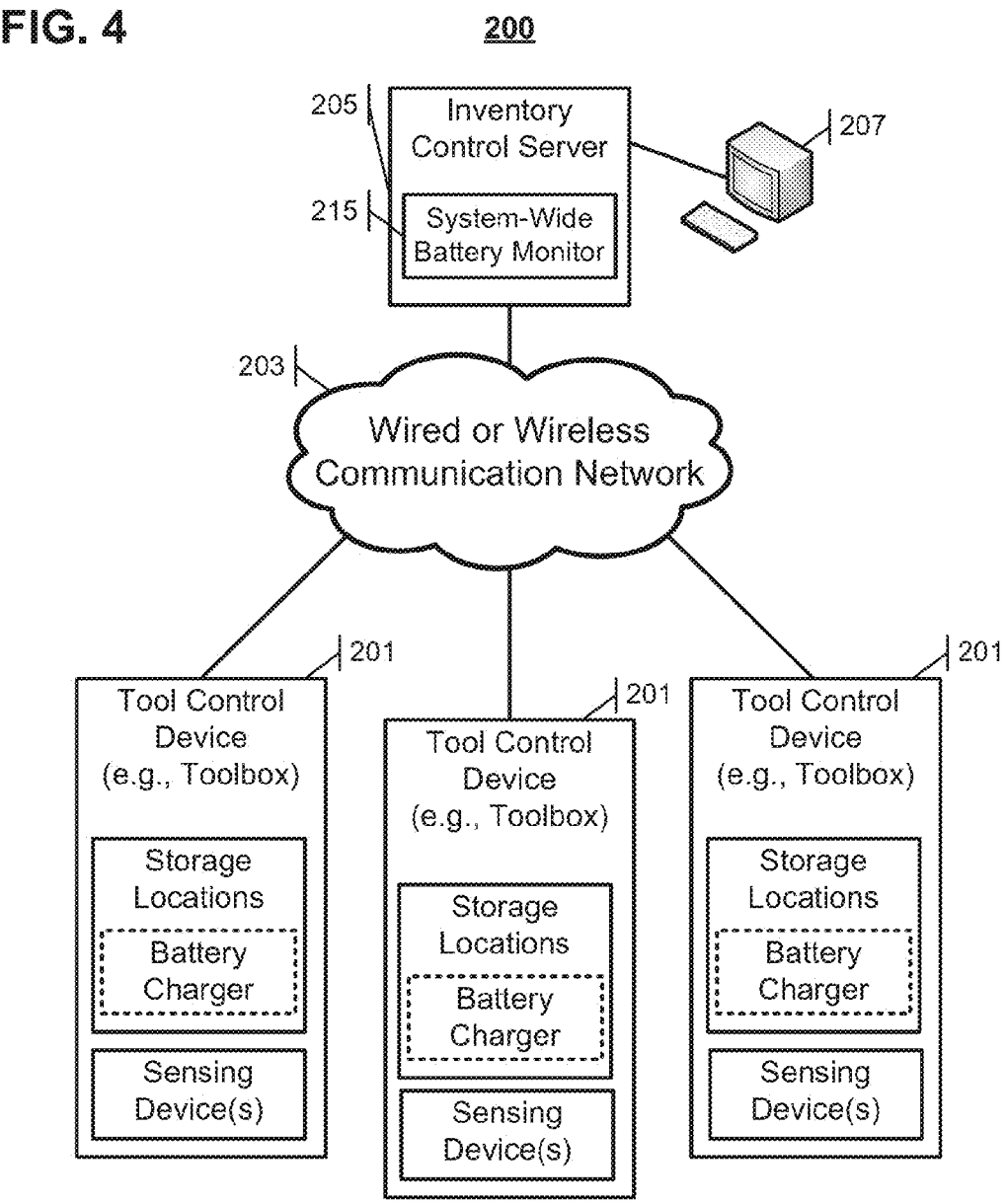
FIG. 4 shows a high-level functional block diagram of a networked automated tool control system including multiple automated tool control devices communicatively connected to each other.

In some examples, such as the example of FIG. 4, a tool control system (e.g., 100) can form part of a networked tool control system that includes multiple tool control devices. For example, as shown in FIG. 4, a networked tool control system 200 can include a plurality of tool control devices 201 which each may be similar to the tool control system 100 of FIGS. 2A and 3A so as to each include storage locations, sensing devices, and one or more battery chargers therein. The tool control devices 201 may be communicatively connected to each other and/or to an inventory control server 205 via a wired or wireless communication network 203. A system administrator terminal 207 may be connected to the server 205 to enable a system administrator to manage the system as needed and receive alerts from the system. In this manner, the processor and memory storing executable program instructions of any individual tool control device 201 can be connected to the computer network (e.g., 203) and exchange data with an administrative software application running on the server 205 and used to manipulate and store data and store and display information relative to the data to system users. The administrative software application running on the server 205 can include a system wide battery monitor 215 which maintains a database storing usage data and battery status monitoring data (e.g., charging data) on individual batteries, battery packs, and tools stored in all tool control devices 201 of the networked tool control system 200. The usage data and charging data can include time stamps indicating when charging of batteries, battery packs, and tools started and/or ended (e.g., corresponding to time stamps indicating when the batteries, battery packs, and tools were placed in chargers, removed from chargers, or when chargers were activated, de-activated, or indicated that charging was complete). The charging data can also include data on the charge and discharge rates of the batteries, battery packs, and tools which can be determined based on a type of battery, battery pack, or tool, and/or based on records of the charging and/or discharging history of the batteries, battery packs, and tools.

Figure 5:
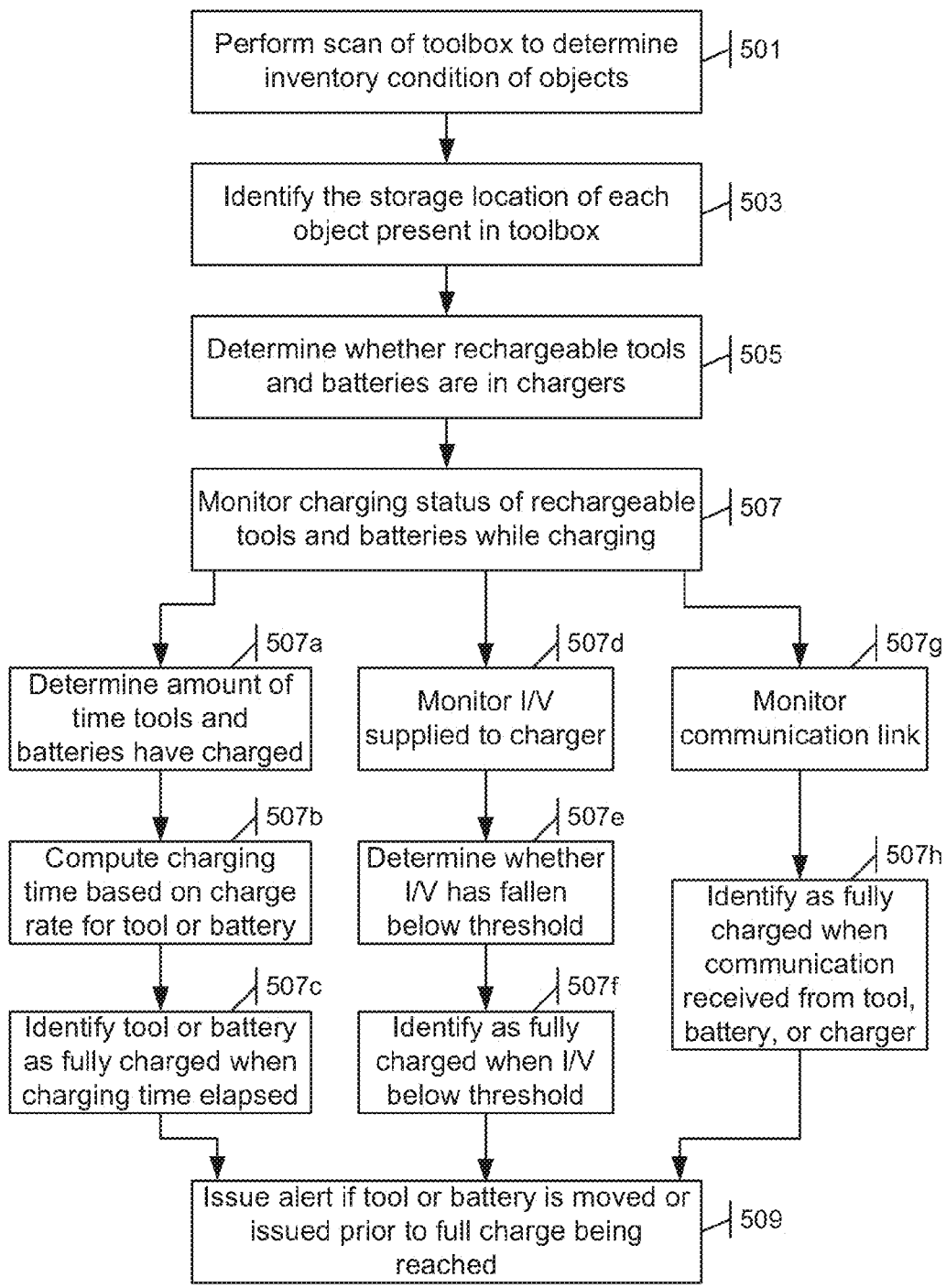
FIG. 5 shows a flow diagram illustrating inventory control and battery status monitoring functionalities provided by the automated tool control system described herein.

As discussed above in relation to FIG. 3A, the automated tool control system 100 includes a data processing system 140 storing executable program instructions stored in a non-transitory machine readable storage medium which, when executed on the processor, cause the data processing system (and the automated tool control system 100) to perform tool control and asset management functionalities. FIG. 5 is a flow diagram showing illustrative functions performed by the automated tool control system 100.

As part of its operation method 500, the automated tool control system 100 performs a scan of storage locations of the automated tool control system to determine an inventory condition in step 501. For example, the data processing system 140 determines the presence and absence of inventory objects (e.g., tools, batteries, and battery packs) in the tool control system 100 using methods similar to those described above. Step 501 may be triggered by a user logging into the automated tool control system, a user opening or closing a drawer or door of the tool control system, or the step can be triggered on a periodic basis or remotely by a tool control system administrator, for example. The performing of the scan involves activating the sensing system 150 and capturing sensing data related to the presence or absence of any tools, batteries, battery packs, chargers, and/or other inventory items. For example, the sensing data may be image data showing whether storage locations have tools or other inventory items therein, and showing tags or unique identifiers of tools and other inventory items that are present in the storage locations. The sensing data can alternatively include data on RFID tags, bar code tags, or other identifiers detected within the automated tool control system, or other appropriate sensing data depending on the type of the sensing system 150 in use. The processing system 140 processes the sensing data based on stored data identifying objects associated with the automated tool control system (e.g., based on image data, RFID or other tag data, or the like stored in non-transitory memory), and identifies the tools and objects present in the storage locations on the basis of the processing.

As part of determining inventory conditions, the processing system 140 commonly identifies in step 503 the drawer, shelf, cabinet, and/or particular storage locations in which is located each tool or inventory item that is identified as being present in the tool control system. By cross-referencing with a database of tools, batteries, and other inventory items, the processing system can thus determine whether or not an inventory item that was returned to a particular storage location (or, more generally, to a particular tool control system 100) is assigned to that storage location (or that tool control system 100) or another storage location (or tool control system). The processing system 140 can issue an alert to the user through the display screen 105 or other user interface when the object does not belong in the storage location or tool control system 100 to which it has been returned. The alert can also be provided to a system administrator remote from the tool control system 100.

The processing system 140 can, as part of identifying the physical storage locations of inventory items inside the tool control system 100, determine whether a rechargeable tool, battery, or battery pack identified as being present in the tool control system 100 is located in a battery slot 147/21 of a battery charger 145/20 (e.g., in the side cabinet 133) or is otherwise being recharged, or whether the tool, battery, or battery pack is located in another storage location (e.g., in a storage location 121 within one of the drawers 130) where it is not being recharged (step 505).

In general, upon determining that a rechargeable tool, battery, or battery pack is returned to the tool control system 100, the processing system 140 identifies the tool, battery, or battery pack as being discharged. For example, the processing system 140 may create an entry in the database including a time stamp identifying the return of the tool, battery, or battery pack to the tool control system and including a flag identifying the tool, battery, or battery pack as being discharged.

In turn, the processing system 140 may monitor the charging of the tool, battery, or battery pack (step 507) in order to appropriately update the flag identifying the tool, battery, or battery pack as being discharged based on the system's monitoring of the charging status of the tool, battery, or battery pack while it is stored in the inventory control system. For example, the processing system 140 uses data including the time stamp and physical location of the object within the three dimensional storage space to determine the length of time the object (e.g., a rechargeable tool, battery, or battery pack) has been stored in the battery charger (step 507a).

In turn, the processing system uses predetermined data on a charge rate for the object to compute (or estimate) the time required for the object to be fully charged when in the battery charger (step 507b), and updates the flag identifying the object as being discharged to a flag identifying the object as being fully charged when the object is determined to have been present in the battery charger for the calculated time (step 507c). The data on charge rates may be input into the system by a user, retrieved from a network-connected server, or established based on data on charge times for the object determined according to historic data stored in the database on previous recharging of the object by the system.

The processing system further provides alerts to users in step 509 when an object is removed or issued from the inventory control system, or is moved from the battery charger to another storage location in the inventory control system 100, prior to the object having reached full charge (e.g., prior to the object having had adequate time to reach full recharge while in the battery charger). In this way, the user is notified that the rechargeable tool, battery, or battery pack may have limited remaining charge and the user may decide to retrieve a different tool or battery from the inventory control system.

In these ways, the processing system 140 uses time stamp data associated with the issue and return of the object, combined with data on the physical storage location of the object during each time interval between time stamps (e.g., whether the object was stored in the charger vs. in a storage drawer), to determine if the object is being returned from usage or if the object has instead been moved from one storage location (e.g., in the charger) to a different storage location (e.g., in a drawer) without having been put to use. The processing system 140 can thus selectively issue alerts to the user and system administrator when the object is determined to have been returned from usage directly to a storage location (e.g., in the drawer) without having previously been placed in the battery charger. The alert may be issued when the battery is returned or when it is next issued, and may indicate that the battery may not be fully charged.

The processing system 140 and sensing system 150 are generally configured to uniquely identify inventory items (e.g., tools, batteries, battery parks or the like) present in the tool control system 100. For example, tags located on inventory items and including unique identifiers can be used to distinguish between inventory items that are otherwise visually identical, and the processing system 140 can thus, through the detection of the tags, distinguish between visually identical inventory items as part of its inventory control functions. The processing system 140 can thus use data obtained from combined sensing technologies (e.g., in cases in which multiple sensing system(s) 150 are used, such as distinct sensing systems used for inventory management and battery status monitoring) to determine charge status of specific tools or batteries through unique identification of the tools or batteries (e.g., using identifiers on the batteries) located in chargers. The charge status is further determined by the processing system 140 based on color and/or activity of status indicators (e.g., LEDs, lights, or displays) on the inventory items or on the battery chargers. For example, a flashing red light may indicate that a tool or battery is currently charging, while a steady green light may indicate that a tool or battery has reached full charge. The processing system 140 can thus, based on the monitoring of the status indicators, alert users and system administrators of battery charge status for batteries stored in the battery chargers. The processing system 140 can further uniquely track inventory items that are relocated within the tool control system (e.g., relocated to a storage drawer from a charger following the object reaching full charge), and can thus accurately identify the objects as being fully charged even when they are moved from a charger to another storage location within the tool storage system 100.

Note that while the foregoing description has focused on an illustrative example in which status indicators such as LEDs or lights are used, other battery status monitoring sensors can be used. For example, the charge status of an object may be determined based on I/V sensing by monitoring the current or voltage supplied to a tool, battery, battery pack, or battery pack during charging of the tool, battery, or battery pack (step 507*d*). A full charge may then be determined when the current being drawn by (or voltage being supplied to) a battery charger falls below a predetermined threshold (steps 507*e*-507*f*). In another example, the charge status of an object may be determined based on a communication received from a "smart" tool, battery, or charger. In such examples, the processing system 140 may establish a communication link with a tool, battery, or charger across a wired or wireless link, and may monitor the communication link by listening for communications from the tool, battery or charger across the link (step 507*g*). A full charge may be determined when the processing system 140 receives a communication from the tool, battery, or charge indicating that full charge has been reached (step 507*h*). The wired or wireless link can be used to obtain other information in the processing system 140, including data on battery performance that may be gathered by a microcontroller of the tool or battery and communicated through wired and/or wireless links to the communication-based sensing system 150 of the automated tool control system 100.

An illustrative example of the tool storage and control system 100 is described in further detail below.

In the example, the tool storage and control system 100 takes the form of a physically defined, secure three dimensional object storage device which is the container from which the inventory items or objects (e.g., tools, batteries, battery packs, or the like) are issued and/or returned. The object storage device has a section with drawers (e.g., disposed one over the other) and a section with a hinged door. The tool storage and control system 100 further includes shelves or drawers in the section with the hinged door, and AC power is provided at least inside the section with the hinged door for powering battery chargers stored therein.

The tool storage and control system 100 is equipped with a processor and non-transitory memory storing executable program instructions for causing the processing to communicate electronically directly or through a network with sensing devices and obtain data from sensing devices relative to the presence, absence, and location of inventory objects, and relative to status of chargers within the tool storage system 100. The status of chargers can be tracked by sensing color and/or activity of indicator lights of the chargers or of the rechargeable inventory objects stored therein within the tool storage and control system 100. The status of chargers can be tracked through other means, such as I/V sensing and/or communication with chargers and tools configured for wired or wireless communication.

The sensing devices used within the tool storage and control system 100 can include machine vision identification sensors such as cameras, used in combination with unique identifiers encoded in tags affixed to inventory objects present in the tool storage and control system 100.

Alternatively, the sensing devices used within the tool storage and control system 100 includes machine vision identification with cameras, machine vision identification with cameras and unique identifiers encoded in tags affixed to inventory objects present in the tool storage and control system 100, and RFID antennas and readers and unique identifiers encoded in RFID tags affixed to inventory objects present in the tool storage and control system 100. The sensing devices can thus uniquely identify the tools or other inventory items present in the tool storage and control system 100, and can identify the storage location in which each identified tool or inventory item is present.

Additionally, so-called "Smart" battery technology may be used, in combination with unique imaging or RFID identifiers, to electronically provide battery status related data, and presence, absence and location data within the drawers and side cabinet.

The tool storage and control system 100 is equipped with at least one electronically controlled locking mechanism, along with a processor and machine readable instructions configured to electronically identify a user requesting access to the secure area or object storage device. The processor may further be configured to identify predetermined authorized access levels to the system and allow or deny physical access by a user to the three dimensional space or object storage and control device based on those predetermined authorized levels of access. The systems used to electronically identify users requesting access are RFID proximity sensors with cards.

In the example, the tool storage and control system 100, and in particular its processor, is communicatively connected to a computer network and is configured to exchange (transmit and receive) data with an administrative software application server used to manipulate and store data and store and display information relative to the data to system users.

The tool storage and control system 100 includes a display and a network connection both of which can be used to display information to users on inventory objects' statuses (e.g., present or absent from the tool storage system) and tools, batteries, and battery packs' charging statuses. The system also displays data on physical locations of the inventory objects when stored in the drawers or in the hinged door section with shelves or drawers, and estimated charge levels of batteries stored within the storage and control device. The system also provides user and system administrator alerts when the batteries may not be fully charged, and when an object not belonging to the storage device is placed in the storage and control device. The system further provides periodic (e.g., scheduled) charging status reports for serialized batteries (and/or tools and battery packs) stored in automated tool control system, wherein the batteries, battery packs, and tools are identified by unique item number (e.g., serial number). The reports provide information on object locations and on historical data on charging cycles of the batteries. The reports can be displayed on a display of the automated tool control system, and/or delivered to a system administrator (e.g., via a network connection).

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. An automated tool control system comprising:
a plurality of storage locations including one storage location configured to store a rechargeable inventory item and another storage location configured to store a tool;
a charger associated with the one storage location of the plurality of storage locations and configured to charge the rechargeable inventory item when the rechargeable inventory item is present in the one storage location; and
a processor and sensing device configured to determine the presence or absence of inventory items, including the rechargeable inventory item and the tool, in the plurality of storage locations,
wherein the processor is configured to determine presence of the rechargeable inventory item including a removable rechargeable battery with a plurality of time stamps and the one storage location associated with the charger, to monitor a charging status of at least one rechargeable inventory item, to determine presence of the at least one rechargeable inventory item in the other storage location, and to selectively issue an alert to a user with the at least one rechargeable inventory item in the other storage location.

2. The automated tool control system of claim 1, wherein the at least one rechargeable inventory item is at least one of a rechargeable tool, battery, and battery pack.

3. The automated tool control system of claim 1, wherein the processor and sensing device are further configured to determine whether the charger is charging the at least one rechargeable inventory item.

4. The automated tool control system of claim 3, wherein the sensing device is an imaging-based sensing device configured, in coordination with the processor, to sense presence or absence of inventory items, including the rechargeable inventory item and the tool, in the plurality of storage locations, and the processor and sensing device are configured to determine a color or status of an indicator of the charger or at least one rechargeable inventory item.

5. The automated tool control system of claim 3, wherein the sensing device includes a current or voltage sensing device configured to sense a current or voltage of the charger.

6. The automated tool control system of claim 1, wherein the processor is configured for wired or wireless communication with the charger or at least one rechargeable inventory item, and receives information indicative of the charging status of the at least one rechargeable inventory item through the wired or wireless communication with the charger or at least one rechargeable inventory item.

7. The automated tool control system of claim 6, wherein the rechargeable inventory item includes a battery and a microprocessor gathering battery performance information during use of the battery, and the processor further receives information on performance of the battery through the wired or wireless communication.

8. The automated tool control system of claim 1, wherein the processor determines an amount of time that the at least one rechargeable inventory item is present in the one storage location associated with the charger, and determines a charging status of the at least one rechargeable inventory item based on the determined amount of time.

9. The automated tool control system of claim 8, wherein the automated tool control system stores a charge rate for the at least one rechargeable inventory item, and the processor determines the charging status of the at least one rechargeable inventory item based on the determined amount of time and the stored charge rate.

10. The automated tool control system of claim 1, wherein the plurality of storage locations further includes another storage location separate from the one storage location associated with the charger and configured to store the at least one rechargeable inventory item, and
wherein the processor and sensing device are configured to determine the presence of the at least one rechargeable inventory item in the other storage location.

11. The automated tool control system of claim 10, wherein when the at least one rechargeable inventory item is determined to be present in the automated tool control system, the processor is configured to distinctly identify presence of the at least one rechargeable inventory item in the one storage location associated with the charger and in the other storage location.

12. The automated tool control system of claim 1, wherein the processor is configured to maintain a database in non-transitory memory storing the plurality of time stamps each associated with at least one of a respective time at which the at least one rechargeable inventory item has been determined to be present in the one storage location associated with the charger and a respective time at which the at least one rechargeable inventory item has been determined to be absent from the one storage location associated with the charger, and
wherein the processor is configured to estimate a charge status of the at least one rechargeable inventory item based on the stored plurality of time stamps.

13. The automated tool control system of claim 12, wherein the processor is configured to estimate the charging status of the at least one rechargeable inventory item based on a charge rate of the at least one rechargeable inventory item.

14. The automated tool control system of claim 12, wherein the processor is further configured to selectively issue the alert to a system administrator when the estimated charging status of the at least one rechargeable inventory item reaches a full charge.

15. The automated tool control system of claim 1, wherein the processor and sensing device are further configured to monitor an indicator of the charger or the at least one rechargeable inventory item indicative of a charging status of the charger or the at least one rechargeable inventory item, and
wherein the processor is configured to report to a user a charging status of the at least one rechargeable inventory item based on the monitoring of the indicator.

16. The automated tool control system of claim 15, wherein the indicator includes at least one light emitting diode (LED) whose lighting status, lighting color, or lighting activity is indicative of the charging status of the at least one rechargeable inventory item.

17. The automated tool control system of claim 1, further comprising:
a plurality of drawers, each drawer including at least one storage location of the plurality of storage locations; and
at least one cabinet having a hinged door and including at least another storage location of the plurality of storage locations,
wherein the charger is disposed in the at least one cabinet.

18. A method for monitoring a rechargeable inventory item in an automated tool control system, comprising:
determining, using a processor and sensing device of the automated tool control system, presence or absence of the rechargeable inventory item including a removable rechargeable battery with a plurality of time stamps and of a tool in a plurality of storage locations of the automated tool control system including one storage location configured to store the rechargeable inventory item and another storage location configured to store the tool;
upon determining presence of the tool in the plurality of storage locations, identify, using the processor and sensing device, the storage location of the plurality of storage location in which the tool is present;
upon determining presence of the rechargeable inventory item in the plurality of storage locations, determining presence of the rechargeable inventory item in one storage location associated with a charger configured to charge the rechargeable inventory item when the at least one inventory item is present in the one storage location;
upon determining presence of the rechargeable inventory item in the one storage location associated with the charger, monitoring a charging status of the rechargeable inventory item; and
selectively issue an alert to a user with the at least one rechargeable inventory item in the other storage location.

19. The method for monitoring a charging status of claim 18, wherein the monitoring the charging status of the rechargeable inventory item comprises monitoring activity of the charger having the one storage location with the rechargeable inventory item present therein through at least one of imaging-based sensing, current sensing, and voltage sensing.

20. The method for monitoring a charging status of claim 18, wherein the monitoring the charging status of the rechargeable inventory item comprises receiving information indicative of the charging status of the rechargeable inventory item through a wired or wireless communication link between the processor and the charger or rechargeable inventory item.

21. The method for monitoring a charging status of claim 18, wherein the monitoring the charging status of the rechargeable inventory item comprises determining an amount of time during which the rechargeable inventory item is present in the one storage location associated with the charger, and determining a charging status of the rechargeable inventory item based on the determined amount of time.

\* \* \* \* \*